United States Patent

Gala et al.

[11] Patent Number: 5,905,152
[45] Date of Patent: May 18, 1999

[54] PREPARATION OF AMINOMETHYL-PHENYLIMIDAZOLES

[75] Inventors: Dinesh Gala, East Brunswick, N.J.; Ingrid Mergelsberg, Dagmersellen, Switzerland; Martin Steinman, Livingston, N.J.; Brigitte Giesinger, Lucerne; Dominik Scherer, Horw, both of Switzerland

[73] Assignee: Schering Corporation, Kenilworth, N.J.

[21] Appl. No.: 08/907,118

[22] Filed: Aug. 6, 1997

Related U.S. Application Data

[60] Provisional application No. 60/024,676, Aug. 8, 1996.

[51] Int. Cl.⁶ .................. C07D 403/12; C07D 403/14; C07D 403/04; C07D 403/00
[52] U.S. Cl. .................. 544/295; 544/333; 544/370; 548/335.5; 548/341.5; 548/342.5
[58] Field of Search .................. 548/335.5, 341.5, 548/342.5; 544/370, 333, 295

[56] References Cited

U.S. PATENT DOCUMENTS

| | | | |
|---|---|---|---|
| 5,034,539 | 7/1991 | Arrang et al. | 548/335.5 |
| 5,055,588 | 10/1991 | Takase et al. | 548/344 |
| 5,159,083 | 10/1992 | Thurkauf et al | 548/335.5 |
| 5,633,377 | 5/1997 | Thurkauf et al. | 544/370 |
| 5,719,169 | 2/1998 | Kleemann et al. | 514/357 |

FOREIGN PATENT DOCUMENTS

| | | |
|---|---|---|
| 92/12134 | 7/1992 | WIPO . |
| 96/10018 | 4/1996 | WIPO . |
| 96/16040 | 5/1996 | WIPO . |

OTHER PUBLICATIONS

J. March, "Advanced Organic Chemistry," John Wiley & Sons, New York (1985), p. 311, line 26–p. 312, line 8.

*Primary Examiner*—Floyd D. Higel
*Attorney, Agent, or Firm*—Palaiyur Kalyanaraman; Arthur Mann

[57] ABSTRACT

Aminomethyl-phenylimidazoles are produced by reaction of an ester of a hydroxymethyl-phenylimidazole with an amine. A particularly preferred ester is the acetate ester. The aminomethyl-phenylimidazoles have useful properties as highly selective partial agonists or antagonists at brain dopamine receptor subtypes. A preferred compound prepared is 5-fluoro-2-[4-[(2-phenyl-1H-imidazol-5-yl)methyl]-1-piperazinyl]pyrimidine. Esters of the hydroxymethyl-phenylimidazoles are useful intermediates.

14 Claims, No Drawings

PREPARATION OF AMINOMETHYL-PHENYLIMIDAZOLES

This application claims the benefit of U.S. Provisional Application, Serial No. 60/024,676, filed Aug. 8, 1996.

FIELD OF THE INVENTION

This invention relates to a novel process for the preparation of aminomethyl-phenylimidazoles having useful properties as highly selective partial agonists or antagonists at brain dopamine receptor subtypes or as prodrugs thereof, in particular to the preparation of 5-fluoro-2-[4-[(2-phenyl-1H-imidazol-5-yl)methyl]-1-piperazinyl]pyrimidine and its pharmaceutically acceptable acid addition salts. This invention also relates to novel intermediates useful in this process.

BACKGROUND OF THE INVENTION

U.S. Pat. No. 5,159,083 (Thurkauf et al., Assignors to Neurogen Corporation) describes and claims aminomethyl-phenylimidazole derivatives as a class of dopamine receptor subtype specific ligands. Similar compounds are described in PCT publications WO 92/12134 (which largely corresponds to U.S. Pat. No. 5,159,083), WO 96/10018 and WO 96/16040. Such compounds show promise in the treatment of psychoses such as schizophrenia, and also in the treatment of psychomotor disturbances such as Parkinsonism.

A subgroup of compounds covered by formula I of U.S. Pat. No. 5,159,083 comprises phenylimidazolylmethylpiperazines, and a particularly preferred compound of this type that is covered by formula I of U.S. Pat. No. 5,159,083 but not specifically disclosed therein is 5-fluoro-2-[4-[(2-phenyl-1H-imidazol-5-yl)methyl]-1-piperazinyl]pyrimidine, a compound having the formula A:

(A)

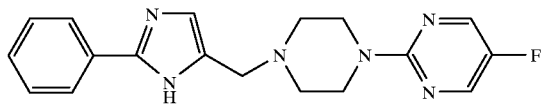

This compound is disclosed in WO 96/16040 as compound 58 on page 37 and (as its dihydrochloride) in Example 9 at page 55 lines 22–23, where an alternative name, 2-phenyl-4(5)-[(4-(5-fluoro-2-pyrimidinyl)-piperazin-1-yl)methyl]-imidazole, is given. Another preferred compound is the corresponding des-fluoro derivative, 2-[4-[(2-phenyl-1H-imidazol-5-yl)methyl]-1-piperazinyl]pyrimidine.

A general chemical method is described in the above-cited U.S. patent and PCT publications for the preparation of aminomethyl-phenylimidazole derivatives; in U.S. Pat. No. 5,159,083 it is shown in Scheme I across columns 11 and 12. The important steps (in relation to the process of the present invention) are those at the last arrow of Scheme I, namely the chlorination of the 5-hydroxymethyl-2-(optionally substituted phenyl)-1H-imidazole with thionylchloride to yield the corresponding 5-chloromethyl compound, which is then allowed to react with an amine to yield a desired aminomethyl-phenylimidazole, e.g., a phenylimidazolylmethylpiperazine. For the preparation of the compound of formula A, this can be shown in Scheme A as follows:

Scheme A

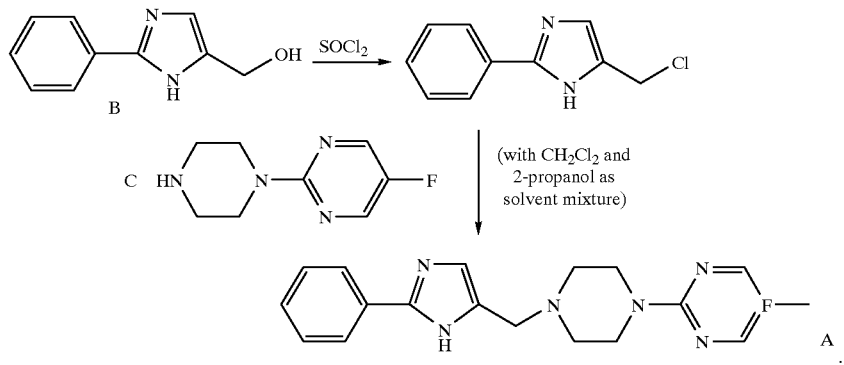

However, that process, especially as applied to the compound of the formula A, has a number of disadvantages:

1. The chloromethyl intermediate is unstable and reactive;
2. It is therefore difficult to purify, extremely so by recrystallization;
3. It is consequently difficult to scale up the processes for its preparation and further conversion;
4. Its condensation with 5-fluoro-2-piperazinyl-pyrimidine proceeds in relatively low yield, especially in larger scale preparations;
5. The desired product, 5-fluoro-2-[4-[(2-phenyl-1H-imidazol-5-yl)methyl]-1-piperazinyl]pyrimidine, is not easy to purify from that process.

Another possible process for the preparation of compounds of this type comprises the fusion of compounds similar to the hydroxy compound of the formula B and the amino compound of the formula C in Scheme A above. This process is illustrated in WO 96/16040 in Scheme 3 on page 45 and in Example 39 (part B) for 2-[4-[(2-phenyl-1H-imidazol-5-yl)methyl]-1-piperazinyl]pyrimidine. However, this process affords only about an 80% yield of 2-[4-[(2-phenyl-1H-imidazol-5-yl)methyl]-1-piperazinyl]pyrimidine and consumes a large amount (two equivalents or more) of the compound of formula C; moreover, it does not afford a practical yield of the compound of the formula A itself.

Some of these disadvantages tend to apply similarly in the preparation of other compounds of this series.

Clearly, methods are needed that avoid or reduce these disadvantages and provide a process for the preparation of aminomethyl-phenylimidazoles that affords the final product in greater yield and purity, proceeds from an intermediate that is easier to handle, especially to purify, and is better suited to preparation on the commercial scale.

SUMMARY OF THE INVENTION

The present invention provides such a process and intermediates useful therein.

The present invention provides a process for the preparation of a compound of the formula:

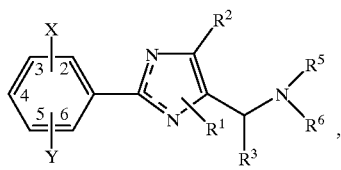

(II)

and the pharmaceutically acceptable acid addition salts thereof, wherein:

X and Y, which may be the same or different, are hydrogen or halogen atoms, or alkyl or alkoxy groups, or one of them at the 3- or 5-position can represent $SO_2R^4$ or $SO_2NHR^4$ wherein $R^4$ is alkyl, or one of them at the 4-position can represent dialkylamino;

$R^1$ is a hydrogen atom or an alkyl group and is attached to a nitrogen atom of the imidazole ring;

or X at the 2-position and $R^1$ represent —$(CH_2)_n$-, wherein n is 1, 2 or 3;

$R^2$ is a hydrogen atom or an alkyl group;

$R^3$ is a hydrogen atom or an alkyl group;

$R^5$ and $R^6$, which may be the same or different, are hydrogen, or alkyl or aralkyl, or $R^5$ and $R^6$ together can represent —$(CH_2)_p$-, wherein p is 2 or 3;

or $R^5$ and $R^6$ together with the adjacent nitrogen atom can represent a 2-(1,2,3,4-tetrahydro)isoquinolinyl group, or a 2-(1,2,3,4-tetrahydro)isoquinolinyl group carrying one or two substituents selected from the group consisting of halogen, hydroxy, alkyl and alkoxy, or a group of the formula

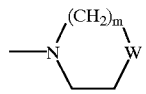

wherein m is 0, 1 or 2, W is O, S, $CHR^7$ or $NR^7$, wherein $R^7$ is hydrogen or a phenyl, pyridinyl or pyrimidinyl group, or a phenyl, pyridinyl or pyrimidinyl group carrying one or more substituents selected from the group consisting of halogen, hydroxy, alkyl and alkoxy; and the dotted lines in the imidazole ring indicate a single bond to the nitrogen atom that carries $R^1$ and a double bond to the nitrogen atom that does not carry $R^1$;

which comprises condensing a compound of the formula

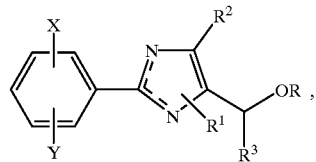

(III)

wherein X, Y, $R^1$, $R^2$, $R^3$ and the dotted lines are as defined above;

and R is an acyl group of an alkanoic acid, an aromatic carboxylic acid, an aralkanoic acid, or an alkane- or aromatic-sulfonic acid;

with a compound of the formula $$NHR^5R^6 \quad IV,$$

wherein $R^5$ and $R^6$ are as defined above;

in the presence of an organic solvent.

The invention further provides compounds of the formula

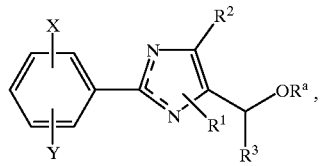

(IIIa)

and the acid addition salts thereof, wherein $R^1$, $R^2$, X, Y, and the dotted lines are as defined above, and $R^a$ is an acyl group of an alkanoic acid, an aromatic carboxylic acid, or an aralkanoic acid. These compounds are useful intermediates in the above process, and can be prepared according to the invention by acylation of a compound of the formula III wherein R is H with an acylating agent.

A novel salt of 5-fluoro-2-[4-[(2-phenyl-1H-imidazol-5-yl)methyl]-1-piperazinyl]pyrimidine provided by the present invention is its dimethanesulfonate.

DETAILED DESCRIPTION OF THE PREFERRED EMBODIMENTS

Compounds of the formula III wherein R is an acyl group as defined above are stable and easy to prepare in good yield from the corresponding alcohols (compounds of the formula III wherein R is H) by standard acylation methods. They are easy to purify, e.g., by recrystallization. They react smoothly with compounds of the formula IV to yield compounds of the formula II in good yield and purity.

Compounds of formula III or IIIa wherein $R^1$ is hydrogen are tautomeric, since such a hydrogen atom is not bonded specifically to either nitrogen atom of the imidazole ring but can migrate from one to the other. All such tautomers fall within formula III or IIIa. Similarly, compounds of the formula II wherein $R^1$ is hydrogen are tautomeric; the compound of the formula A can also exist in tautomeric forms.

In the present specification and claims, the various terms listed below have the following meanings unless otherwise indicated:

"Halogen" indicates fluorine, chlorine, bromine or iodine.

"Alkyl" indicates a saturated, straight or branched-chain, hydrocarbon group containing from 1 to 6 carbon atoms (e.g., methyl, ethyl, propyl, 2-propyl, butyl, 2-butyl, pentyl and hexyl), and the same definition applies to the 'alkyl' part of "alkoxy"; "lower alkyl" indicates such groups containing from 1 to 4 carbon atoms.

"Alkanoyl" indicates a formyl group or an alkylcarbonyl group wherein the alkyl group is as defined above (e.g., propionyl, butyryl, pentanoyl, or hexanoyl), but is preferably acetyl.

"Aromatic" (in relation to an aromatic carboxylic or aromatic-sulfonic acid) indicates a benzene or naphthalene nucleus that may carry one or two substituents selected from the group consisting of halogen atoms and alkyl and alkoxy groups (preferably unsubstituted phenyl, 4-chlorophenyl or 4-tolyl).

"Aralkyl" indicates an aryl-alkyl group wherein the aryl group is an aromatic group as defined above (preferably phenyl or substituted phenyl) substituting an alkyl group as defined above (preferably methyl or ethyl).

"Aralkanoic" indicates an aryl-alkyl-carbonyl group wherein the aryl group is an aromatic group as defined above (preferably phenyl or substituted phenyl) substituting an alkyl group as defined above (preferably methyl or ethyl).

DMSO, DMF, and THF indicate dimethylsulfoxide, N,N-dimethylformamide and tetrahydrofuran respectively.

Preferred alkyl and alkoxy groups include methyl, methoxy, ethyl and ethoxy groups.

R (in the compound of formula III) may be for example an alkane- or aromatic-sulfonyl group such as methanesulfonyl, ethanesulfonyl, benzenesulfonyl, 4-chlorobenzenesulfonyl, or 4-toluenesulfonyl, or an acyl group of an aromatic carboxylic or aralkanoic acid such as benzoyl, 4-chlorobenzoyl, 4-methylbenzoyl, or phenylacetyl, but is preferably a lower alkanoyl group such as formyl, propionyl, or butyryl, or especially acetyl.

A particularly preferred group of compounds of the present invention has the formula II wherein:

X and Y, which may be the same or different, are hydrogen or halogen atoms, or lower alkyl or lower alkoxy groups;

$R^1$ is a hydrogen atom or a methyl group and is attached to a nitrogen atom of the imidazole ring;

$R^2$ is a hydrogen atom or a lower alkyl group;

W is CH or N;

$R^3$ is a hydrogen atom; and $R^5$ and $R^6$ together with the adjacent nitrogen atom represent a group of the formula

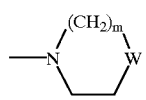

wherein m is 0, 1 or 2, W is $CHR^7$ or $NR^7$, wherein $R^7$ is hydrogen or a phenyl, pyridinyl or pyrimidinyl group, or a phenyl, pyridinyl or pyrimidinyl group carrying one or more substituents selected from the group consisting of halogen, hydroxy, alkyl and alkoxy. W is most preferably $NR^7$. A pyridinyl or pyrimidinyl group in $R^7$ is preferably a 2-pyridinyl or 2-pyrimidinyl group, which may carry one or more substituents selected from the group consisting of halogen, hydroxy, lower alkyl and lower alkoxy. $R^7$ is preferably a group of the formula

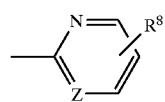

wherein Z is N or CH and $R^8$ is halogen, hydroxy, lower alkyl or lower alkoxy. $R^7$ is most preferably a group of the formula

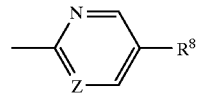

wherein Z is CH or preferably N and $R^8$ is halogen, hydroxy, lower alkyl or lower alkoxy; $R^8$ is most preferably fluorine.

The reaction between the compounds of formula III and IV is preferably carried out with an excess of an organic or inorganic base. The organic base is preferably a tertiary organic base, especially a trialkylamine, e.g., a tri(lower alkyl)amine such as dimethylethylamine, triethylamine, tripropylamine, tri(2-propyl)amine, N,N-di(2-propyl) ethylamine or tributylamine. Triethylamine is effective and is especially preferred on account of its availability and low cost. If desired, a strong tertiary organic base can also be added, e.g., N,N-dimethylaminopyridine, preferably in a small amount (e.g., 2–10% of the trialkylamine). The inorganic base can be for example a hydroxide, carbonate or bicarbonate of sodium or potassium. An inert organic solvent can be used (although a large excess of the tertiary organic base can serve as solvent), e.g., an aromatic hydrocarbon such as benzene or toluene, a chlorinated hydrocarbon solvent such as $CH_2Cl_2$, a polar organic solvent such as DMSO or DMF, or an ether such as dioxane or THF. The reaction is effected at ambient or moderately elevated temperature, e.g., at 40–70° C., preferably 50–60° C., until the reaction is complete (typically 3–5 hours at 50–60° C.). The product of the formula II can then be isolated by standard techniques, e.g., by adding water and filtration, or extraction with a water-immiscible organic solvent. It can be isolated as the free base or as a pharmaceutically acceptable acid addition salt; the free base can if desired be converted into a pharmaceutically acceptable acid addition salt. Preferred salts include the dihydrochloride and the dimethane-sulfonate.

The imidazole starting material of the formula III can be prepared by acylation of the corresponding hydroxymethyl compound (wherein R is H) with an appropriate acylating agent. The acylating agent can be for example an acid halide or even the acid itself in the presence of an appropriate ester-forming reagent such as a carbodiimide, but is preferably the acid anhydride $R_2O$, or more preferably $R^a{}_2O$ (wherein R and $R^a$ are as defined for formulae III and IIIa respectively), which can be used in a small excess, e.g., 5–20% excess, preferably 8–12% excess. When the acylating agent is simply the acid anhydride, no base is necessary. Otherwise a tertiary alkylamine such as triethylamine can be used as base. The product of the formula III can then be isolated by standard techniques, e.g., by cooling and filtration if it precipitates, or by adding water if the solvent is water-miscible and filtration of a precipitate or extraction with a water-immiscible organic solvent.

5-Hydroxymethyl-2-phenyl-1H-imidazole and 5-fluoro-2-piperazinylpyrimidine are available commercially.

5-Acetoxymethyl-2-phenyl-1H-imidazole is a superior reagent to 5-chloromethyl-2-phenyl-1H-imidazole since it is very stable and is readily purified by simple methods like recrystallization; moreover, its condensation with 5-fluoro-2-piperazinylpyrimidine proceeds smoothly and cleanly to afford 5-fluoro-2-[4-[(2-phenyl-1H-imidazol-5-yl)methyl]-1-piperazinyl]pyrimidine in high yield and purity. For these reasons, 5-acetoxymethyl-2-phenyl-1H-imidazole is much more readily prepared, purified and used on the commercial scale than 5-chloromethyl-2-phenyl-1H-imidazole.

5-Fluoro-2-[4-[(2-phenyl-1H-imidazol-5-yl)methyl]-1-piperazinyl]pyrimidine is very advantageously administered in pharmaceutical compositions as its dihydrochloride, which we have isolated in a single reproducible polymorphic form. Another advantageous salt for this purpose is the dimethanesulfonate, which also forms reproducibly in a single polymorphic form. These are more advantageous forms for use in pharmaceutical compositions than the dimaleate, which exists in two polymorphic forms having different physical properties, either of which may form. Furthermore, both the dihydrochloride and the dimethanesulfonate are significantly more soluble in water than the dimaleate and are thus more readily available upon oral administration.

EXAMPLE

The following Example serves to illustrate the present invention.

Step I

Preparation of 5-Acetoxymethyl-2-phenyl-1H-imidazole

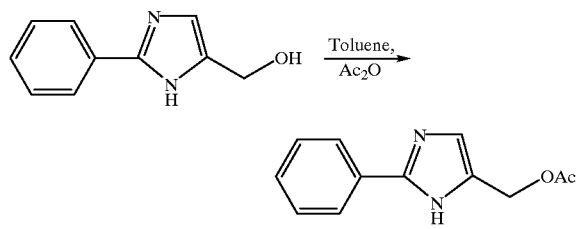

Mix 5-hydroxymethyl-2-phenyl-1H-imidazole (1.3 Kg) and toluene (10.4 L) at 20–25° C., and then heat the mixture with stirring to 50–55° C. Add acetic anhydride (780 ml, 1.1 equivalents) slowly and continue heating at 50–55° C. until the reaction is complete (typically 3–4 hours). Cool the reaction mixture to −5–0° C., filter off the product, wash it with toluene (3×700 ml) and then dry it under vacuum at 50–55° C. to constant weight.

Yield of free base: about 1.7 Kg (90%), at least 98% pure by HPLC; m.p. 146.4° C. (dec.), MS 225 (MH$^+$).

Step II

Preparation of 5-Fluoro-2-[4-[(2-phenyl-1H-imidazol-5-yl)methyl]-1-piperazinyl]pyrimidine

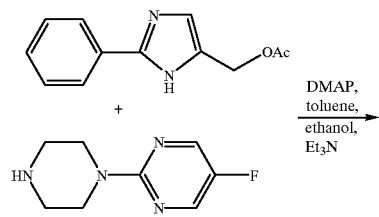

-continued

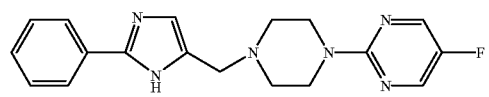

Mix 5-fluoro-2-piperazinyl-pyrimidine (900 g), 5-acetoxymethyl-2-phenyl-1H-imidazole (1.17 Kg, 1.1 equivalents), DMAP (N,N-dimethylaminopyridine, 30 g), toluene (7.2 L), ethanol (1.8 L) and triethylamine (1.095 L) at 20–25° C., and heat the mixture with stirring at 50–55° C. until the reaction is complete (typically about 20–25 hours). Then add water (3.75 L) and cool the resulting suspension to 0–50° C. Filter off the product, wash it with water (6×1.4 L) and cold toluene (3×700 ml), and dry it under vacuum at 50–55° C. to constant weight.

Yield: about 1.55 Kg (92%), more than 99% pure by HPLC; m.p. 146.4° C. (DSC, dec.), MS: 339 (MH$^+$).

Step III

Preparation of 5-Fluoro-2-[4-[(2-phenyl-1H-imidazol-5-yl)methyl]-1-piperazinyl]pyrimidine dihydrochoride Dissolve 5-fluoro-2-[4-[(2-phenyl-1H-imidazol-5-yl)methyl]-1-piperazinyl]pyrimidine (25 g) in dry ethanol (250 ml) at reflux (75–80° C.). Add decolorizing carbon (1.25 g), stir the black suspension for 20–30 minutes and filter off the carbon.

Add concentrated (aqueous) HCl (13.5 ml) to the filtrate at 55–60° C., cool the solution to 20–25° C. over a period of 30–40 minutes and then further cool it to 0–5° C. and store it at that temperature for two hours. Filter off the solid with suction and wash it with ethanol (25 ml).

Yield: 28 g (93%), at least 99% pure; starts to decompose at 190° C. or higher (the decomposition temperature depends upon the rate of heating).

The salt can be recrystallized from ethanol.

Step IV

Preparation of 5-Fluoro-2-[4-[(2-phenyl-1H-imidazol-5-yl)methyl]-1-piperazinyl]pyrimidine di-methanesulfonate Suspend 5-fluoro-2-[4-[(2-phenyl-1H-imidazol-5-yl)methyl]-1-piperazinyl]pyrimidine (0.5 g) in ethanol (6 ml) at 55–60° C. Add methanesulfonic acid (0.21 ml) and stir the mixture for 30 minutes. Cool it to 0–5° C. and filter to obtain 0.7 g (90%) of the di-mesylate salt, m.p. 228–230° C. (dec.).

All publications and patent applications cited herein are incorporated by reference to the same extent as if each individual publication or patent application was specifically and individually indicated to be incorporated by reference.

While a number of embodiments of this invention are described herein, it is apparent that the embodiments can be altered to provide other embodiments that utilize the compositions and processes of this invention. Therefore, it will be appreciated that the scope of this invention includes alternative embodiments and variations which are defined in the foregoing Specification; and the invention is not to be limited to the specific embodiments that have been presented herein by way of example.

We claim:

1. A process for the preparation of a compound of the formula:

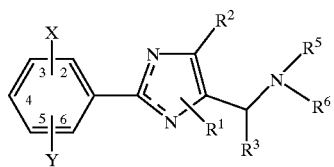

or a pharmaceutically acceptable acid addition salts thereof, wherein:

X and Y, which is therefor the same or different, are selected from the group consisting of hydrogen, halogen, alkyl group and alkoxy group, further wherein when one of said X and Y is at the 3- or 5-position said X or Y represents $SO_2R^4$ or $SO_2NHR^4$ where $R^4$ is alkyl, and when one of said X and Y is at the 4-position said X or Y represents a dialkylamino;

$R^1$ is a hydrogen or an alkyl group and is attached to a nitrogen atom of the imidazole ring; or when X is at the 2-position then $R^1$ and X together represent —$(CH2)_n$-, wherein n is 1, 2 or 3;

$R^2$ is a hydrogen or an alkyl group;

$R^3$ is a hydrogen or an alkyl group;

$R^5$ and $R^6$, which may be the same or different, are hydrogen, alkyl, aralkyl, or $R^5$ and $R^6$ together represent —$(CH2)_p$-, wherein p is 2 or 3; or the moiety $NR^5R^6$ jointly represents a 2-(1,2,3,4-tetrahydro)isoquinolyl group said isoquinolyl group is unsubstituted or substituted by one or two substituents selected from the group consisting of halogen, hydroxy, alkyl, alkoxy, and a group of the formula:

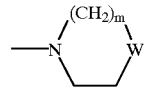

wherein m is 0, 1 or 2, W is O, S, $CHR^7$ or $NR^7$, wherein $R^7$ is hydrogen, phenyl, pyridinyl or pyrimidinyl group, said phenyl, pyridyl or pyrimidinyl group optionally carrying one or more substituents selected from the group consisting of halogen, hydroxy, alkyl and alkoxy; and the dotted lines in the imidazole ring indicate a single bond to the nitrogen atom that carries $R^1$ and a double bond to the nitrogen that does not carry $R^1$;

said process comprising:
reacting a compound of the formula:

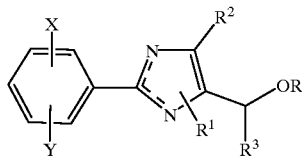

wherein X, Y, $R^1$, $R^2$, $R^3$, and the dotted lines are as defined above; and R is an acyl group of an alkanoic acid, an aromatic carboxylic acid, an aralkanoic acid, an alkane-sulfonic acid or an aromatic-sulfonic acid; with a compound of the formula:

$NHR^5R^6$      IV wherein $R^5$ and $R^6$ are as defined above, in an organic solvent at temperatures from ambient to about 70° C. for times up to about 25 hours.

2. The process of claim 1 wherein R is a lower alkanoyl group.

3. The process of claim 2 wherein R is an acetyl group.

4. The process of claim 1 wherein the reaction is carried out in the presence of an excess of an organic or inorganic base.

5. The process of claim 4 wherein said organic base is a tertiary organic base.

6. The process of claim 5 wherein the tertiary organic base is triethylamine.

7. The process of claim 1, wherein said organic solvent is an inert organic solvent.

8. The process of claim 7 wherein the inert organic solvent is an aromatic hydrocarbon, a chlorinated hydrocarbon solvent, a polar organic solvent, or an ether.

9. The process of claim 8 wherein the organic solvent is benzene, toluene, $CH_2Cl_2$, DMSO, DMF, dioxane or THF.

10. The process of claim 1, wherein, in the compounds of formulae II and III:

X and Y, which may be the same or different, are hydrogen, halogen, lower alkyl group or lower alkoxy group and $R^2$ is hydrogen or a lower alkyl group;

and, in the compounds of formulae II and IV:

$R^3$ is hydrogen; and the moiety $NR^5R^6$ jointly represents a group of the formula:

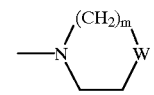

wherein m is 0, 1 or 2, W is O, S, $CHR^7$ or $NR^7$, wherein $R^7$ is hydrogen, phenyl, pyridinyl or pyrimidinyl group, said phenyl, pyridyl or pyrimidinyl group being unsubstituted or substituted by one or more substituents selected from the group consisting of halogen, hydroxy, alkyl and alkoxy.

11. The process of claim 10 wherein W is $NR^7$ wherein $R^7$ is a 2-pyridinyl or 2-pyrimidinyl group, said 2-pyridinyl or 2-pyrimidinyl group being unsubstituted or substituted by one or more substituents selected from the group consisting of halogen, hydroxy, lower alkyl and lower alkoxy.

12. The process of claim 11 wherein $R^7$ is a group of the formula

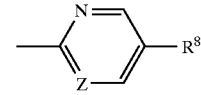

wherein Z is CH or N and $R^8$ is halogen, hydroxy, lower alkyl or lower alkoxy.

13. The process of claim 12 wherein Z is N and $R^8$ is fluorine.

14. The process of claim 1 wherein the compound of the formula III is prepared by acylating a compound of the formula

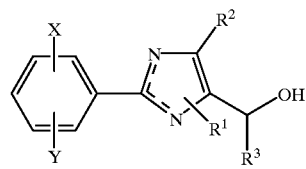

wherein the dotted lines, $R^1$, $R^2$, X and Y are as defined in claim 1.

* * * * *